(12) United States Patent
Lang et al.

(10) Patent No.: US 6,576,024 B1
(45) Date of Patent: Jun. 10, 2003

(54) MIXTURE FOR THE OXIDATION TINTING OF KERATIN FIBRES CONTAINING A LACCASE AND TINTING METHOD USING SAID MIXTURE

(75) Inventors: Gérard Lang, Saint Prix (FR); Jean Cotteret, Verneuil sur Seine (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/600,102

(22) PCT Filed: Jan. 12, 1999

(86) PCT No.: PCT/FR99/00038

§ 371 (c)(1),
(2), (4) Date: Oct. 2, 2000

(87) PCT Pub. No.: WO99/36045

PCT Pub. Date: Jul. 22, 1999

(30) Foreign Application Priority Data

Jan. 13, 1998 (FR) ............................................. 98 00249

(51) Int. Cl.$^7$ ................................................. A61K 7/13
(52) U.S. Cl. ........................ 8/405; 8/405; 8/406; 8/407; 8/408; 8/409; 8/411; 8/412
(58) Field of Search ........................... 8/406, 407, 408, 8/409, 411, 412, 405

(56) References Cited

U.S. PATENT DOCUMENTS 5,976,195 A * 11/1999 de la Mettrie et al. ......... 8/411

FOREIGN PATENT DOCUMENTS

WO    WO-9719998    *  6/1997

* cited by examiner

*Primary Examiner*—Yogendra N. Gupta
*Assistant Examiner*—Eisa Elhilo
(74) *Attorney, Agent, or Firm*—Finnegan, Henderson Farabow, Garrett and Dunner, LLP

(57) ABSTRACT

The invention relates to a cosmetic mixture for the oxidation tinting of keratin fibres, containing in a support material suitable for tinting keratin fibres (a) at least one laccase-type enzyme; (b) at least one polymer thickener selected from the group constituted by: (i) amphiphilic non-ionic polymers comprising at least one fatty chain and at least one hydrophilic unit; (ii) anionic amphiphilic polymers comprising at least one hydrophilic unit and at least one fatty chain unit; (iii) cross-linked acrylic acid homopolymers; (iv) cross-linked 2-acrylamide-2-methyl-propane sulfonic acid homopolymers and their cross-linked acrylamide copolymers, which are partially or fully neutralized; (v) ammonium acrylate homopolymers or ammonium acrylate and acrylamide copolymers; (vi) dimethylaminoethyl-methacrylate homopolymers quatemized by methyl chloride or dimethylaminoethyl-methacrylate copolymers quaternized by methyl chloride and acrylamide copolymers; (vii) non-ionic guar gums; (viii) scleroglucan gum (a biopolysaccharide of microbial origin): (ix) gums made of vegetable exudates such as gum arabic, gum ghatti, gum karaya and gum tragacanth; and (c) at least one oxidation tint. The invention also relates to the tinting methods making use of the above mixture.

70 Claims, No Drawings

MIXTURE FOR THE OXIDATION TINTING OF KERATIN FIBRES CONTAINING A LACCASE AND TINTING METHOD USING SAID MIXTURE

The subject of the present invention is a composition for the oxidation dyeing of keratinous fibres comprising at least one enzyme of the laccase type, at least one oxidation dye and at least one thickening polymer, as well as its uses for dyeing keratinous fibres, in particular human hair.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in Patent U.S. Pat. No. 3,251,742, Patent Applications FR-A-2,112,549, FR-A-2,694,018, EP-A-0,504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The Applicant has surprisingly discovered novel compositions containing, as oxidizing system, at least one enzyme of the laccase type and at least one particular thickening polymer which will be defined in more detail below, capable of constituting in the presence of oxidation dyes, ready-to-use dyeing formulations leading to colours which are more homogeneous, more intense and more chromatic without causing significant degradation or decolouring of the keratinous fibres, exhibiting low selectivity and good resistance to various attacks to which the hair may be subjected.

These discoveries form the basis of the present invention.

The first subject of the present invention is therefore a ready-to-use composition intended for the oxidation dyeing of keratinous fibres, in particular human keratinous fibres and more particularly human hair, comprising, in a carrier appropriate for dyeing keratinous fibres:

(a) at least one enzyme of the laccase type;
(b) at least one thickening polymer chosen from the group consisting of:
  (i) nonionic amphiphilic polymers comprising at least one fatty chain and at least one hydrophilic unit;
  (ii) anionic amphiphilic polymers comprising at least one hydrophilic unit and at least one fatty chain-containing unit;
  (iii) crosslinked homopolymers of acrylic acid;
  (iv) crosslinked homopolymers of 2-acrylamido-2-methylpropanesulphonic acid and their crosslinked copolymers of acrylamide which are partially or completely neutralized;
  (v) homopolymers of ammonium acrylate or the copolymers of ammonium acrylate and of acrylamide;
  (vi) homopolymers of dimethylaminoethyl methacrylate which is quaternized with methyl chloride or copolymers of dimethylaminoethyl methacrylate which is quaternized with methyl chloride and of acrylamide;
  (vii) nonionic guar gums;
  (viii) scleroglucan gums (biopolysaccharide of microbial origin),
  (ix) gums derived from plant exudates such as gum arabic, Ghatti gum, karaya gum and tragacanth gum;
(c) at least one oxidation dye.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense*, in the extracts of Podocarpaceae, *Rosmarinus off., Solanum tuberosum*, Iris sp., Coffea sp., *Daucus carrota, Vinca minor, Persea americana, Catharenthus roseus*, Musa sp., *Malus pumila, Gingko biloba, Monotropa hypopithys* (Indian pipe), Aesculus sp., *Acer pseudoplatanus, Prunus persica, Pistacia palaestina*.

Among the laccases of fungal origin optionally obtained by biotechnology which can be used according to the invention, there may be mentioned the laccase(s) derived from *Polyporus versicolor, Rhizoctonia practicola* and *Rhus vernicifera* as indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae*, or variants thereof. There may also be mentioned those derived from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The lacu unit corresponds to the quantity of enzyme catalysing the conversion of 1 mmol of syringaldazine per minute at pH 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The lacu unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in lacu units.

The quantities of laccase used in the compositions of the invention will vary according to the nature of the laccase chosen. Preferably, they will vary from 0.5 to 2000 lacu, or from 1000 to $4 \times 10^7$ u units, or from 20 to $2 \times 10^6$ ulac units per 100 g of composition.

Among the thickening polymers according to the present invention, the nonionic amphiphilic polymers comprising at least one fatty chain and at least one hydrophilic unit are preferably chosen from:
(1) Celluloses modified with groups comprising at least one fatty chain; there may be mentioned by way of example:
   hydroxyethylcelluloses modified with groups comprising at least one fatty chain such as alkyl, arylalkyl or alkylaryl groups or mixtures thereof, and in which the alkyl groups are preferably $C_8-C_{22}$, such as the product NATROSOL PLUS GRADE 330 CS ($C_{16}$ alkyls) sold by the company AQUALON, or the product BERMOCOLL EHM 100 sold by the company BEROL NOBEL,
   those modified with polyalkylene glycol alkylphenyl ether groups, such as the product AMERCELL POLYMER HM-1500 (polyethylene glycol (15) nonylphenyl ether) sold by the company AMERCHOL.
(2) Hydroxypropylguars modified with groups comprising at least one fatty chain such as the product ESAFLOR HM 22 ($C_{22}$ alkyl chain) sold by the company LAMBERTI, the products MIRACARE XC95-3 ($C_{14}$ alkyl chain) and RE205-1 ($C_{20}$ alkyl chain) sold by the company RHONE POULENC.
(3) Polyurethane ethers comprising at least one fatty chain such as $C_8-C_{30}$ alkyl or alkenyl groups, such as the products DAPRAL T 210 and DAPRAL T 212 sold by the company AKZO.
(4) Copolymers of vinylpyrrolidone and of hydrophobic monomers containing a fatty chain; there may be mentioned by way of example:
   the products ANTARON V216 or GANEX V216 (vinylpyrrolidone/hexadecene copolymer) sold by the company I.S.P.
   the products ANTARON V220 or GANEX V220 (vinylpyrrolidone/eicosene copolymer) sold the company I.S.P.
(5) Copolymers of $C_1-C_6$ alkyl methacrylates or acrylates and of amphiphilic monomers comprising at least one fatty chain such as for example the oxyethylenated methyl methacrylate/stearyl acrylate copolymer sold by the company GOLDSCHMIDT under the name ANTIL 208.
(6) Copolymers of hydrophilic methacrylates or acrylates and of hydrophobic monomers comprising at least one fatty chain, such as for example the polyethylene glycol methacrylate/lauryl methacrylate copolymer.

Among the anionic amphiphilic polymers according to the invention comprising at least one hydrophilic unit and at least one unit containing a fatty chain, there are preferred those comprising at least one allyl ether unit containing a fatty chain and at least one hydrophilic unit consisting of an unsaturated ethylenic anionic monomer, more particularly of a vinylcarboxylic acid and most particularly of an acrylic acid, a methacrylic acid or mixtures thereof, the allyl ether unit containing a fatty chain corresponding to the monomer of the following formula (1):

$$CH_2=CR'CH_2OB_nR \qquad (1)$$

in which R' denotes H or $CH_3$, B denotes an ethyleneoxy radical, n is zero or denotes an integer ranging from 1 to 100, R denotes a hydrocarbon radical chosen from alkyl, arylalkyl, aryl, alkylaryl or cycloalkyl radicals comprising 8 to 30 carbon atoms, preferably 10 to 24 and still more particularly from 12 to 18 carbon atoms.

A unit of formula (I) which is more particularly preferred according to the present invention is a unit in which R' denotes H, n is equal to 10, and R denotes a stearyl ($C_{18}$) radical.

Anionic amphiphilic polymers of this type are described and prepared according to a method of polymerization in emulsion in patent EP-0216479 B2.

Among these anionic amphiphilic polymers, there are particularly preferred according to the invention the polymers formed from 20 to 60% by weight of acrylic acid and/or methacrylic acid, from 5 to 60% by weight of lower alkyl (meth)acrylates, from 2 to 50% by weight of allyl ether containing a fatty chain of formula (I), and from 0 to 1% by weight of a crosslinking agent which is a well known copolymerizable polyethylenic unsaturated monomer, such as diallyl phthalate, allyl (meth)acrylate, divinylbenzene, (poly)ethylene glycol dimethacrylate and methylenebisacrylamide.

Among the latter, there are most particularly preferred the crosslinked terpolymers of methacrylic acid, of ethyl acrylate, of polyethylene glycol (10 EO) stearyl alcohol ether (Steareth 10), in particular those sold by the company ALLIED COLLOIDS under the names SALCARE SC 80 and SALCARE SC90 which are aqueous 30% emulsions of a crosslinked terpolymer of methacrylic acid, of ethyl acrylate and of steareth-10-allyl ether (40/50/10).

The anionic amphiphilic polymers may also be chosen from those comprising at least one hydrophilic unit of the olefinic unsaturated carboxylic acid type, and at least one hydrophobic unit exclusively of the ($C_{10}$–$C_{30}$)alkyl ester of unsaturated carboxylic acid type, which are used according to the invention, are preferably chosen from those whose hydrophilic unit of the olefinic unsaturated carboxylic acid type corresponds to the monomer of the following formula (2)

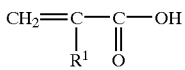  (2)

in which formula $R^1$ denotes H or $CH_3$ or $C_2H_5$ (that is to say acrylic acid, methacrylic acid or ethacrylic acid units and in which the hydrophobic unit of the ($C_{10}$–$C_{30}$)alkyl ester of unsaturated carboxylic acid type corresponds to the monomer of the following formula (3):

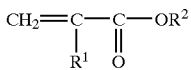  (3)

in which formula $R^1$ denotes H or $CH_3$ or $C_2H_5$ (that is to say acrylate, methacrylate or ethacrylate units) and preferably H (acrylate units) or $CH_3$ (methacrylate units), $R^2$ denoting a $C_{10}$–$C_{30}$, and preferably $C_{12}$–$C_{22}$, alkyl radical.

($C_{10}$–$C_{30}$)Alkyl esters of unsaturated carboxylic acids in accordance with the invention comprise for example lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are for example described and prepared according to patents U.S. Pat. Nos. 3,915,921 and 4,509,949.

The anionic amphiphilic polymers which can be used in the context of the present invention can denote more particularly polymers formed from a mixture of monomers comprising:

(i) essentially acrylic acid, an ester of the following formula (3):

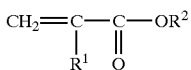  (3)

in which $R^1$ denotes H or $CH_3$, $R^2$ denoting an alkyl radical having from 12 to 22 carbon atoms, and a crosslinking agent, such as for example those consisting of 95 to 60% by weight of acrylic acid (hydrophilic unit), 4 to 40% by weight of $C_{10}$–$C_{30}$ alkyl acrylate (hydrophobic unit), and 0 to 6% by weight of crosslinking polymerizable monomer, or 98 to 96% by weight of acrylic acid (hydrophilic unit), 1 to 4% by weight of $C_{10}$–$C_{30}$ alkyl acrylate (hydrophobic unit), and 0.1 to 0.6% by weight of crosslinking polymerizable monomer, (ii) essentially acrylic acid and lauryl methacrylate such as that formed from 66% by weight of acrylic acid and 34% by weight of lauryl methacrylate.

The said crosslinking agent is a monomer containing a group

with at least one other polymerizable group whose unsaturated bonds are not conjugated with respect to each other. There may be mentioned in particular the polyallyl ethers such as in particular polyallylsucrose and polyallylpentaerythritol.

Among the said above polymers, there are most particularly preferred according to the present invention the products sold by the company GOODRICH under the trade names PEMULEN TR1, PEMULEN TR2, CARBOPOL 1382, and still more preferably PEMULEN TR1, and the product sold by the company S.E.P.C. under the name COATEX SX.

Among the crosslinked homopolymers of acrylic acid which can be used in the context of the present invention there may be mentioned those crosslinked with an allyl ether of an alcohol of the sugar series, such as for example the products sold under the names CARBOPOLS 980, 981, 954, 2984 and 5984 by the company GOODRICH or the products sold under the names SYNTHALEN M and SYNTHALEN K by the company 3 VSA;

Among the crosslinked homopolymers of 2-acrylamido-2-methylpropanesulphonic acid, there may be mentioned those described in application EP-A-0815828 (which forms an integral part of the content of the description). Among the crosslinked copolymers of 2-acrylamido-2-methylpropanesulphonic acid and of acrylamide which are partially or completely neutralized (with a base such as sodium hydroxide, potassium hydroxide or an amine), there may be mentioned in particular the product described in Example 1 of the document EP-A-503,853 (which forms an integral part of the content of the description).

Among the homopolymers of ammonium acrylate, there may be mentioned the product sold under the name MICROSAP PAS 5193 by the company HOECHST. Among the copolymers of ammonium acrylate and of acrylamide, there may be mentioned the product sold under the name BOZEPOL C NOUVEAU or the product PAS 5193 sold by the company HOECHST (they are described and prepared in the documents FR 2,416,723, U.S. Pat. No. 2,798,053 and U.S. Pat. No. 2,923,692);

Among the homopolymers of dimethylaminoethyl methacrylate which is quaternized with methyl chloride, there may be mentioned the products sold under the names SALCARE 95 and SALCARE 96 by the company ALLIED COLLOIDS. Among the copolymers of dimethylaminoethyl methacrylate, which is quaternized with methyl chloride and of acrylamide, there may be mentioned the product SALCARE SC92 sold by ALLIED COLLOIDS or the product PAS 5194 sold by HOECHST (they are described and prepared in the document EP-A-395,282).

The unmodified nonionic guar gums are for example the products sold under the name VIDOGUM GH 175 by the company UNIPECTINE and under the name JAGUAR C by the company MEYHALL.

The nonionic guar gums which can be used according to the invention are preferably modified with $C_1$–$C_6$ hydroxyalkyl groups.

Among the hydroxyalkyl groups, there may be mentioned by way of example the hydroxymethyl, hydroxyethyl, hydroxypropyl and hydroxybutyl groups.

These guar gums are well known in the state of the art and can for example be prepared by reacting corresponding alkene oxides, such as for example propylene oxides, with guar gum so as to obtain a guar gum modified with hydroxypropyl groups.

The hydroxyalkylation rate, which corresponds to the number of alkylene oxide molecules consumed per number of free hydroxyl functions present on the guar gum, preferably varies from 0.4 to 1.2 and.

Such nonionic guar gums optionally modified with hydroxyalkyl groups are for example sold under the trade names JAGUAR HP8, JAGUAR HP60 and JAGUAR HP120, JAGUAR DC 293 and JAGUAR HP 105 by the company RHONE POULENC (MEYHALL) or under the name GALACTASOL 4H4FD2 by the company AQUALON.

The scleroglucan gum (biopolysaccharide of microbial origin), the gums derived-from plant exudates such as gum arabic, Ghatti gum, karaya gum and tragacanth gum are well known to persons skilled in the art and are described in particular in the book by Robert L. DAVIDSON entitled "Handbook of Water soluble gums and resins" published by McGraw Hill Book Company (1980).

The particular thickening polymers of the invention are preferably used in a quantity which may vary from about 0.01 to 10% by weight of the total weight of the dyeing composition applied to the fibres. More particularly, this quantity varies from about 0.1 to 5% by weight.

In the present invention, it is more particularly preferable to use the thickening polymers chosen from the group consisting of:

(i) nonionic amphiphilic polymers comprising at least one fatty chain and at least one hydrophilic unit;

(ii) anionic amphiphilic polymers comprising at least one hydrophilic unit and at least one unit containing a fatty chain;

(iii) crosslinked homopolymers of acrylic acid;

(vi) homopolymers of dimethylaminoethyl methacrylate which is quaternized with methyl chloride or the copolymers of dimethylaminoethyl methacrylate, which is quaternized with methyl chloride, and of acrylamide;

(vii) nonionic guar gums;

and more particularly those chosen from the group consisting of:

(i) nonionic amphiphilic polymers comprising at least one fatty chain and at least one hydrophilic unit;

(ii) anionic amphiphilic polymers comprising at least one hydrophilic unit and at least one unit containing a fatty chain;

(iii) crosslinked homopolymers of acrylic acid.

The nature of the oxidation dye(s) used in the ready-to-use dyeing composition is not critical. They are chosen from oxidation bases and/or couplers The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (I) and their addition salts with an acid:

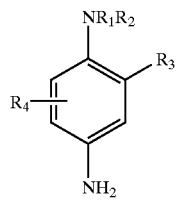

in which:
$R_1$ represents a hydrogen atom, a $C_1$–$C_4$ alkyl radical, a monohydroxy($C_1$–$C_4$ alkyl) radical, a polyhydroxy-($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_2$ represents a hydrogen atom, a $C_1$–$C_4$ alkyl radical, a monohydroxy,($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, $R_4$ represents a hydrogen or halogen atom or a $C_1$–$C_4$ alkyl radical.

Among the nitrogen-containing groups of formula (I) above, there may be mentioned in particular the amino, mono ($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-2-para-phenylenediamine, 2-hydroxymethyl-para-phenylene-diamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylene-diamine, 2,6-dimethyl-para-phenylenediamine, 2,6-diethyl-para-phenylenediamine, 2,3-dimethyl-paraphenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

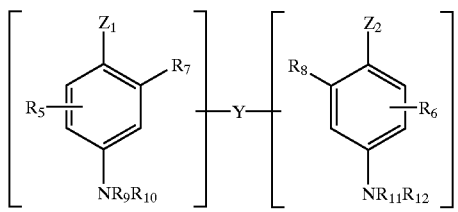

(II)

in which:

$Z_1$ and $Z_2$, which are identical or different, represent a hydroxyl or —$NH_2$ radical which may be substituted with a $C_1$–$C_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a monohydroxy($C_1$–$C_4$ alkyl) radical, a polyhydroxy($C_2$–$C_4$ alkyl) radical, an amino($C_1$–$C_4$ alkyl) radical or a linking arm Y;

$R_7$, $R_8$, $R_9$, $R_{10}$, $R_{11}$ and $R_{12}$, which are identical or different, represent a hydrogen atom, a linking arm Y or a $C_1$–$C_4$ alkyl radical;

it being understood that the compounds of formula (II) contain only one linking arm Y per molecule.

Among the nitrogen-containing groups of formula (II) above, there may be mentioned in particular the amino, mono($C_1$–$C_4$)alkylamino, ($C_1$–$C_4$) dialkylamino, ($C_1$–$C_4$) trialkylamino, monohydroxy($C_1$–$C_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (III), and their addition salts with an acid:

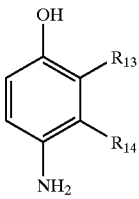

(III)

in which:

$R_{13}$ represents a hydrogen or halogen atom, a $C_1$–$C_4$ alkyl, monohydroxy ($C_1$–$C_4$ alkyl), ($C_1$–$C_4$) alkoxy ($C_1$–$C_4$)-alkyl, amino($C_1$–$C_4$ alkyl) or hydroxy($C_1$–$C_4$) alkylamino-($C_1$–$C_4$ alkyl) radical, $R_{14}$ represents a hydrogen or halogen atom, a $C_1$–$C_4$ alkyl, monohydroxy($C_1$–$C_4$ alkyl), polyhydroxy ($C_2$–$C_4$ alkyl), amino ($C_1$–$C_4$ alkyl), cyano ($C_1$–$C_4$ alkyl) or ($C_1$–$C_4$)alkoxy($C_1$–$C_4$)alkyl radical, it being understood that at least one of the radicals $R_{13}$ or $R_{14}$ represents a hydrogen atom.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88–169,571 and JP 91–333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino- 3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylamino-pyrazole, 3,5-diamino-4-(β-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (IV), their addition salts with an acid or with a base and their tautomeric forms, when a tautomeric equilibrium exists:

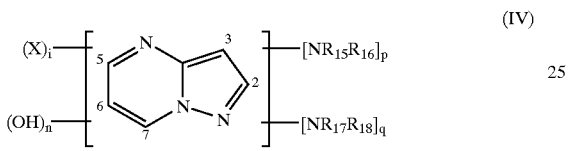

in which:

R$_{15}$, R$_{16}$, R$_{17}$ and R$_{18}$, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a (C$_1$–C$_4$)alkoxy(C$_1$–C$_4$ alkyl) radical, a C$_1$–C$_4$ aminoalkyl radical (it being possible for the amine to be protected with an acetyl, ureido or sulphonyl radical), a (C$_1$–C$_4$)alkylamino(C$_1$–C$_4$ alkyl) radical, a di-[(C$_1$–C$_4$) alkyl]amino (C$_1$–C$_4$ alkyl) radical (it being possible for the dialkyl radicals to form a carbon-containing ring or a 5- or 6-membered heterocycle), a hydroxy(C$_1$–C$_4$)alkyl or di-[hydroxy (C$_1$–C$_4$)alkyl]amino(C$_1$–C$_4$ alkyl) radical, the X radicals, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$) alkylamino(C$_1$–C$_4$ alkyl) radical, a di-[(C$_1$–C$_4$)alkyl] amino(C$_1$–C$_4$ alkyl) radical (it being possible for the dialkyls to form a carbon-containing ring or a 5- or 6-membered heterocycle), a hydroxy(C$_1$–C$_4$)alkyl or di-[hydroxy(C$_1$–C$_4$)alkyl]amino(C$_1$–C$_4$ alkyl) radical, an amino radical, a (C$_1$–C$_4$)alkyl- or di-[(C$_1$–C$_4$)alkyl] amino radical; a halogen atom, a carboxylic acid group, a sulphonic acid group;

i equals 0, 1, 2 or 3;
p equals 0 or 1;
q equals 0 or 1;
n equals 0 or 1;
with the proviso that:
the sum p+q is different from 0;
when p+q is equal to 2, then n equals 0 and the groups NR$_{15}$R$_{16}$ and NR$_{17}$R$_{18}$ occupy positions (2,3); (5,6); (6,7); (3,5) or (3,7);
when p+q is equal to 1, then n equals 1 and the group NR$_{15}$R$_{16}$ (or NR$_{17}$R$_{18}$) and the OH group occupy positions (2,3); (5,6); (6,7); (3,5) or (3,7).

When the pyrazolo[1,5-a]pyrimidines of formula (IV) above are such that they comprise a hydroxyl group on one of the positions 2, 5 or 7 at the α position with respect to a nitrogen atom, a tautomeric equilibrium exists which is represented for example by the following scheme:

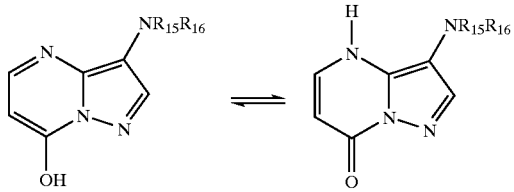

Among the pyrazolo[1,5-a]pyrimidines of formula (IV) above, there may be mentioned in particular:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxy-ethyl)amino]ethanol;
2-[(7-aminopyrazolo[1,5-a]pyrimidin-3-yl)(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5, N7, N7-tetramethylpyrazolo[1,5-a]pyrimidine-3,7-diamine; and their addition salts and their tautomeric forms, when a tautomeric equilibrium exists.

The pyrazolo[1,5-a]pyrimidines of formula (IV) above may be prepared by cyclization from an aminopyrazole according to the syntheses described in the following references:
EP 628559 BEIERSDORF-LILLY
R. Vishdu, H. Navedul, Indian J. Chem., 34b(6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN PHARMACEUTICALS
The pyrazolo[1,5-a]pyrimidines of formula (IV) above can also be prepared by cyclization from hydrazine according to the syntheses described in the following references:
A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) preferably represent from 0.0005 to 12% by weight approximately of the total weight of the dyeing composition in accordance with the invention, and still more preferably from 0.005 to 6% by weight approximately of this weight.

The coupler(s) which can be used in the ready-to-use dyeing composition in accordance with the invention are those conventionally used in oxidation dyeing compositions, that is to say meta-phenylene-diamines, meta-aminophenols, meta-diphenols, heterocyclic couplers, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,14-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The dyeing composition of the invention may also contain, in addition to the oxidation dyes defined above, direct dyes so as to increase the shimmer of the shades. These direct dyes may in particular then be chosen from the nitro, azo or anthraquinone dyes.

The ready-to-use dyeing composition in accordance with the invention may also contain various adjuvants conventionally used in hair dyeing compositions, such as anionic, cationic, nonionic, amphoteric or zwitterionic surfactants or mixtures thereof, polymers, thickeners, antioxidants, enzymes different from the laccases used in accordance with the invention, such as for example peroxidases or oxidoreductases containing 2 electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the ready-to-use dyeing composition in accordance with the invention are not, or substantially not, impaired by the addition(s) envisaged.

The ready-to-use dyeing composition in accordance with the invention can be provided in various forms, such as in the form of liquids, creams, gels, optionally pressurized, or in any other form appropriate for dyeing keratinous fibres, in particular human hair. In this case, the oxidation dye(s) and the laccase(s) are present in the same ready-to-use composition, and consequently the said composition should be free of gaseous oxygen, so as to avoid any premature oxidation of the oxidation dye(s).

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye as defined above and, on the other hand, a composition (B) containing, in a medium appropriate for dyeing, at least one enzyme of the laccase type and at least at least one thickening polymer as defined above, and then in mixing them at the time of use before applying this mixture to the keratinous fibres.

According to a specific embodiment of the invention, the thickening polymer may be incorporated into the composition (A).

Another subject of the invention is a multi-compartment device or dyeing (kit) or any other multi-compartment packaging system in which a first compartment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The medium appropriate for keratinous fibres (or carrier) of the ready-to-use dyeing compositions in accordance with the invention generally consists of water or of a mixture of water and of at least one organic solvent in order to solubilize the compounds which might not be sufficiently soluble in water. As organic solvent, there may be mentioned for example $C_1$–$C_4$ alkanols such as ethanol and isopropanol as well as aromatic alcohols such as benzyl alcohol, similar products and mixtures thereof.

The solvents may be present in proportions preferably of between 1 and 40% by weight approximately relative to the total weight of the dyeing composition, and still more preferably between 5 and 30% by weight approximately.

The pH of the ready-to-use dyeing compositions for the keratinous fibres in accordance with the invention is chosen such that the enzymatic activity of the laccase is not impaired. It generally varies from 4 to 11 approximately, and more preferably from 6 to 9 approximately.

Concrete examples illustrating the invention will now be given.

In the text which follows or in the preceding text, unless otherwise stated, the percentages are expressed by weight.

The following examples illustrate the invention with no limitation being implied.

EXAMPLE 1

Dyeing Composition

The following ready-to-use dyeing composition was prepared (contents in grams).

| | |
|---|---|
| Laccase derived from Rhus vernicifera containing 180 units/mg, marketed by the company SIGMA | 1.8 g |
| ($C_8$—$C_{10}$) alkyl polyglucoside in aqueous solution containing 60% of active substance (AS) sold under the name ORAMIX CG110 by the company SEPPIC | 8.0 g |

-continued

| | |
|---|---|
| Para-phenylenediamine. | 0.254 g |
| 2,4-Diaminophenoxyethanol dihydrochloride | 0.260 g |
| Diurethane HMDI of oxyethylenated (60 EO) and oxypropylenated $C_{16}$—$C_{18}$ alcohol sold under the name DAPRAL T212 by the company AKZO | 1.0 g AS |
| pH agent | qs pH 6.5 |
| Demineralized water | qs 100 g |

This ready-to-use dyeing composition is applied to locks of natural grey hair which is 90% white for 40 minutes at 30° C. The hair is then rinsed, washed with a standard shampoo and then dried.

Locks of hair with bluish-grey colour are obtained.

In this example, 1.8 g of laccase obtained from Rhus vernicifera containing 180 units/mg can be. replaced with 1 g of laccase obtained from Pyricularia Orizae containing 100 units/mg sold by the company I.C.N.

EXAMPLE 2

Dyeing Composition

The following ready-to-use dyeing composition was prepared (content in grams):

| | |
|---|---|
| Laccase derived from Rhus vernicifera containing 180 units/mg, marketed by the company SIGMA | 1.8 g |
| ($C_6$—$C_{10}$) alkyl polyglucoside in aqueous solution containing 60% of active substance (AS) sold under the name ORAMIX CG110 by the company SEPPIC | 8.0 g |
| Para-phenylenediamine | 0.254 g |

This ready-to-use dyeing composition is applied to locks of natural grey hair which is 90% white for 40 minutes at 30° C. The hair is then rinsed, washed with a standard shampoo and then dried.

Locks of hair with bluish-grey colour are obtained.

In this example, 1.8 g of laccase obtained from Rhus vernicifera containing 180 units/mg can be replaced with 1 g of laccase obtained from Pyricularia Orizae containing 100 units/mg sold by the company I.C.N.

What is claimed is:

1. A composition for the oxidation dyeing of keratinous fibers comprising:
   (a) at least one enzyme of the laccase type;
   (b) at least one thickening polymer chosen from:
      (i) nonionic amphiphilic polymers comprising at least one fatty chain and at least one hydrophilic unit;
      (ii) anionic amphiphilic polymers comprising at least one hydrophilic unit and at least one fatty chain-containing unit;
      (iii) crosslinked homopolymers derived from monomers of acrylic acid;
      (iv) crosslinked homopolymers derived from monomers of 2-acrylamido-2-methylpropanesulphonic acid and crosslinked copolymers derived from monomers of acrylamide which are partially or completely neutralized;
      (v) homopolymers derived from monomers of ammonium acrylate and copolymers derived from monomers of (i) ammonium acrylate and (ii) acrylamide;
      (vi) homopolymers derived from monomers of dimethylaminoethyl methacrylate which is quaternized with methyl chloride and copolymers derived from monomers of (i) dimethylaminoethyl methacrylate which is quaternized with methyl chloride and (ii) acrylamide;
      (vii) nonionic guar gums;
      (viii) scleroglucan gums; and
      (ix) gums derived from plant exudates which comprise gum arabic, Ghatti gum, karaya gum and tragacanth gum; and
   (c) at least one oxidation dye.

2. A composition according to claim 1, wherein said keratinous fibers are human keratinous fibers.

3. A composition according to claim 2, wherein said human keratinous fibers are hair.

4. A composition according to claim 1, wherein said at least one enzyme of the laccase type is chosen from laccases of plant origin, animal origin, fungal origin, and bacterial origin and laccases obtained by biotechnology.

5. A composition according to claim 1, wherein said at least one enzyme of the laccase type is chosen from those produced by plants performing chlorophyll synthesis.

6. A composition according to claim 1, wherein said at least one enzyme of the laccase type is chosen from those extracted from plants chosen from Anacardiaceae or Podocarpaceae, *Rosmarinus off.*, *Solanum tuberosum*, Iris sp., Coffea sp., *Daucus carrota*, *Vinca minor*, *Persea americana*, *Catharenthus roseus*, Musa sp., *Malus pumila*, *Gingko biloba*, *Monotropa hypopithys*, Aesculus sp., *Acer pseudoplatanus*, *Prunus persica* and *Pistacia palaestina*.

7. A composition according to claim 1, wherein said at least one enzyme of the laccase type is chosen from those derived from fungi chosen from *Pyricularia orizae*, *Polyporus versicolor*, *Rhizoctonia praticola*, *Rhus vernicifera*, Scytalidium, *Polyporus pinsitus*, *Myceliophtora thermophila*, *Rhizoctonia solani*, *Tramates versicolor*, *Fomes fomentarius*, *Chaetomium thermophile*, *Neurospora crassa*, *Coriolus versicol*, *Botrytis cinerea*, *Rigidoporus lignosus*, *Phellinus noxius*, *Pleurotus ostreatus*, *Aspergillus nidulans*, *Podospora anserina*, *Agaricus bisporus*, *Ganoderma lucidum*, *Glomerella cingulata*, *Lactarius piperatus*, *Russula delica*, *Heterobasidion annosum*, *Thelephora terrestris*, *Cladosporium cladosporioildes*, *Cerrena unicolor*, *Coriolus hirsutus*, *Ceriporiopsis subvermispora*, *Coprinus cinereus*, *Panaeolus papilionaceus*, *Panaeolus sphinctrinus*, *Schizophyllum commune*, *Dichomitius squalens* and variants of all said fungi.

8. A composition according to claim 1, wherein said at least one enzyme of the laccase type is present in a quantity ranging from 0.5 to 2000 lacu units per 100 g of said composition.

9. A composition according to claim 1, wherein said at least one enzyme of the laccase type is present in a quantity ranging from 1000 to $4 \times 10^7$ u units per 100 g of said composition.

10. A composition according to claim 1, wherein said at least one enzyme of the laccase type is present in a quantity ranging from 20 to $2 \times 10^6$ ulac units per 100 g of said composition.

11. A composition according to claim 1, wherein said at least one thickening polymer is chosen from:
    (i) nonionic amphiphilic polymers comprising at least one fatty chain and at least one hydrophilic unit;
    (ii) anionic amphiphilic polymers comprising at least one hydrophilic unit and at least one unit containing a fatty chain;

(iii) crosslinked homopolymers derived from monomers of acrylic acid;
(vi) homopolymers derived from monomers of dimethylaminoethyl methacrylate which is quaternized with methyl chloride, and copolymers derived from monomers of
(i) dimethylaminoethyl methacrylate which is quaternized with methyl chloride and
(ii) acrylamide; and
(vii) nonionic guar gums.

12. A composition according to claim 1, wherein said at least one thickening polymer is chosen from:
   (i) nonionic amphiphilic polymers comprising at least one fatty chain and at least one hydrophilic unit;
   (ii) anionic amphiphilic polymers comprising at least one hydrophilic unit and at least one unit containing a fatty chain; and
   (iii) crosslinked homopolymers derived from monomers of acrylic acid.

13. A composition according to claim 1, wherein said nonionic amphiphilic polymers comprising at least one fatty chain and at least one hydrophilic unit are chosen from nonionic celluloses modified with groups which comprise at least one fatty chain, hydroxypropylguars modified with groups comprising at least one fatty chain, polyurethane ethers comprising at least one fatty chain, copolymers derived from monomers of (i) vinylpyrrolidone and (ii) hydrophobic monomers comprising a fatty chain, copolymers derived from monomers of (i) $C_1$–$C_6$ alkyl methacrylates and/or acrylates and (ii) amphiphilic monomers comprising at least one fatty chain, and copolymers derived from monomers of (i) hydrophilic methacrylates and/or acrylates and (ii) hydrophobic monomers comprising at least one fatty chain.

14. A composition according to claim 1, wherein said anionic amphiphilic polymer comprising at least one hydrophilic unit and at least one fatty chain-containing unit is chosen from anionic amphiphilic polymers comprising at least one allyl ether unit which comprises a fatty chain and at least one hydrophilic unit which comprises a unit derived from an unsaturated ethylenic anionic monomer.

15. A composition according to claim 14, wherein said unsaturated ethylenic anionic monomer is chosen from vinylcarboxylic acids.

16. A composition according to claim 14, wherein said unsaturated ethylenic anionic monomer is chosen from acrylic acid and methacrylic acid.

17. A composition according to claim 14, wherein said at least one allyl ether unit which comprises a fatty chain of said anionic amphiphilic polymer corresponds to a monomer of the following formula (1):

wherein R' is chosen from H and $CH_3$; B is chosen from ethyleneoxy groups, n is an integer ranging from 0 to 100, R is chosen from hydrocarbon groups which comprise at least 8 carbon atoms.

18. A composition according to claim 17, wherein said hydrocarbon groups are chosen from alkyl groups, arylalkyl groups, aryl groups, alkylaryl groups, and cycloalkyl groups wherein all said hydrocarbon groups comprise from 8 to 30 carbon atoms.

19. A composition according to claim 18, wherein said hydrocarbon groups are chosen from alkyl groups, arylalkyl groups, aryl groups, alkylaryl groups, and cycloalkyl groups wherein all said hydrocarbon groups comprise from 10 to 24 carbon atoms.

20. A composition according to claim 19, wherein said hydrocarbon groups are chosen from alkyl groups, arylalkyl groups, aryl groups, alkylaryl groups, and cycloalkyl groups wherein all said hydrocarbon groups comprise from 12 to 18 carbon atoms.

21. A composition according to claim 17, wherein R' is chosen from H, n is 10, and R is chosen from stearyl ($C_{18}$) groups.

22. A composition according to claim 1, wherein said anionic amphiphilic polymer is derived from 20% to 60% by weight of acrylic acid and/or methacrylic acid monomers, 5% to 60% by weight of lower alkyl (meth)acrylate monomers, 2% to 50% by weight of allyl ether monomers which comprise at least one fatty chain of formula (I), and 0% to 1% by weight of a crosslinking agent based on the total weight of said composition.

23. A composition according to claim 22, wherein said crosslinking agent is chosen from copolymerizable polyethylenic unsaturated moomers.

24. A composition according to claim 23, wherein said copolymerizable polyethylenic unsaturated monomers are chosen from diallyl phthalate monomers, allyl (meth)acrylate monomers, divinyl benzene monomers, (poly)ethylene glycol dimethacrylate monomers and methylenebisacrylamide monomers.

25. A composition according to claim 22, wherein said anionic amphiphilic polymer is a crosslinked polymer comprising 40% by weight of units derived from methacrylic acid monomers, 50% by weight of units derived from ethyl acrylate monomers, and 10% by weight of units derived from polyethylene glycol (10 OE) stearyl alcohol (Steareth 10) ether monomers.

26. A composition according to claim 1, wherein said anionic amphiphilic polymer comprises at least one hydrophilic unit derived from olefinic unsaturated carboxylic acid type monomers, and at least one hydrophobic unit derived from ($C_{10}$–$C_{30}$)alkyl esters of unsaturated carboxylic acid type monomers.

27. A composition according to claim 26, wherein said at least one hydrophilic unit derived from olefinic unsaturated carboxylic acid type monomers is chosen from units derived from monomers of the following formula (2):

wherein $R^1$ is chosen from H, $CH_3$ and $C_2H_5$.

28. A composition according to claim 26, wherein said at least one hydrophobic unit derived from $C_{10}$–$C_{30}$ alkyl esters of unsaturated carboxylic acid type monomers corresponds to a unit derived from monomers of the following formula (3)

wherein $R^1$ is chosen from H, $CH_3$,and $C_2H_5$; and $R^2$ is chosen from $C_{10}$–$C_{30}$ alkyl groups.

29. A composition according to claim 28, wherein said $R^2$ is chosen from $C_{12}$–$C_{22}$ alkyl groups.

30. A composition according to claim 28, wherein said at least one hydrophobic unit derived from $C_{10}$–$C_{30}$ alkyl esters of unsaturated carboxylic acid type monomers is derived from monomers chosen from lauryl acrylate, stearyl acrylate, decyl acrylate, isodecyl acrylate, dodecyl acrylate, lauryl methacrylate, stearyl methacrylate, decyl methacrylate, isodecyl methacrylate and dodecyl methacrylate.

31. A composition according to claim 1, wherein said anionic amphiphilic polymer is chosen from polymers derived from monomers of (i) acrylic acid and (ii) monomers of the following formula (3):

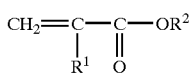

wherein $R^1$ is chosen from H and $CH_3$; $R^2$ is chosen from $C_{12}$–$C_{22}$ alkyl groups and a crosslinking agent.

32. A composition according to claim 31, wherein said anionic amphiphilic polymer is chosen from polymers comprising from 60% to 95% by weight of units derived from acrylic acid monomers, from 4% to 40% by weight of units derived from $C_{10}$–$C_{30}$ alkyl acrylate monomers and from 0% to 6% by weight of units derived from crosslinking polymerizable monomers.

33. A composition according to claim 31, wherein said anionic amphiphilic polymer is chosen from polymers comprising from 96% to 98% by weight of units derived from acrylic acid monomers, from 1% to 4% by weight of units derived from $C_{10}$–$C_{30}$ alkyl acrylate monomers and from 0.1% to 0.6% by weight of units derived from crosslinking polymerizable monomers.

34. A composition according to claim 1, wherein said anionic amphiphilic polymer is chosen from polymers derived from (i) acrylic acid monomers and (ii) lauryl methacrylate monomers.

35. A composition according to claim 34, wherein said anionic amphiphilic polymer is chosen from polymers comprising 66% by weight of units derived from acrylic acid monomers and 34% by weight of units derived from lauryl methacrylate monomers.

36. A composition according to claim 31, wherein said crosslinking agent is chosen from crosslinking agents comprising at least one

group and at least one other polymerizable group wherein said other polymerizable group does not contain unsaturated bonds that are conjugated with respect to each other.

37. A composition according to claim 36, wherein said crosslinking agent is chosen from polyallyl ethers.

38. A composition according to claim 37, wherein said polyallyl ethers are chosen from polyallylsucrose and polyallylpentaerythritol.

39. A composition according to claim 1, wherein said nonionic guar gum is chosen from nonionic guar gums which are modified with at least one $C_1$–$C_6$ hydroxyalkyl group.

40. A composition according to claim 39, wherein said at least one $C_1$–$C_6$ hydroxyalkyl group is chosen from hydroxymethyl groups, hydroxyethyl groups, hydroxypropyl groups and hydroxybutyl groups.

41. A composition according to claim 1, wherein said nonionic guar gums are chosen from nonionic guar gums which exhibit a hydroxyalkylation rate ranging from 0.4 to 1.2.

42. A composition according to claim 1, wherein said at least one thickening polymer is present in a quantity ranging from about 0.01 to about 10% by weight of the total weight of said composition.

43. A composition according to claim 42, wherein said at least one thickening polymer is present in a quantity ranging from about 0.1 to about 5% by weight of the total weight of said composition.

44. A composition according to claim 1, wherein said at least one oxidation dye is at least one oxidation base chosen from para-phenylenediamines, double bases, para-aminophenols, ortho-aminophenols, heterocyclic bases and acid addition salts of all said oxidation bases.

45. A composition according to claim 44, wherein said at least one oxidation base is present in a concentration ranging from 0.0005% to 12% by weight relative to the total weight of said composition.

46. A composition according to claim 45, wherein said at least one oxidation base is present in a concentration ranging from 0.005% to 6% by weight relative to the total weight of said composition.

47. A composition according to claim 44, wherein said acid addition salts are chosen from hydrochlorides, hydrobromides, sulphates, tartrates, lactates and acetates.

48. A composition according to claim 1, wherein said at least one oxidation dye is at least one coupler chosen from meta-phenylenediamines, meta-aminophenols, meta-diphenols, heterocyclic couplers and acid addition salts of all said couplers.

49. A composition according to claim 48, wherein said acid addition salts are chosen from hydrochlorides, hydrobromides, sulphates, tartrates, lactates and acetates.

50. A composition according to claim 48, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and the acid addition salts of all said couplers.

51. A composition according to claim 48, wherein said at least one coupler is present in a concentration ranging from 0.0001% to 10% by weight relative to the total weight of said composition.

52. A composition according to claim 51, wherein said at least one coupler is present in a concentration ranging from 0.005% to 5% by weight relative to the total weight of said composition.

53. A composition according to claim 1, further comprising at least one direct dye.

54. A composition according to claim 53, wherein said at least one direct dye is chosen from nitro, azo and anthraquinone dyes.

55. A composition according to claim 1 further comprising at least one suitable adjuvant chosen from surfactants, polymers, thickening agents different from said at least one thickening agent as defined in claim 35, antioxidants, enzymes different from said at least one enzyme of the laccase type as defined in claim 35, penetrating agents, sequestering agents, perfumes, buffers, dispersing agents, film-forming agents, screening agents, vitamins, preservatives and opacifying agents.

56. A composition according to claim 1, further comprising at least one carrier appropriate for keratinous fibers.

57. A composition according to claim 56, wherein said at least one carrier is chosen from water and at least one organic solvent.

58. A composition according to claim 57, wherein said at least one organic solvent is chosen from lower $C_1$–$C_4$ alcohols and aromatic alcohols.

59. A composition according to claim 57, wherein said at least one organic solvent is present in a concentration ranging from 1% to 40% by weight relative to the total weight of said composition.

60. A composition according to claim 57, wherein said at least one organic solvent is present in a concentration ranging from 5% to 30% by weight relative to the total weight of said composition.

61. A composition according to claim 1 having a pH varying from about 4 to about 11.

62. A composition according to claim 61, wherein said pH varies from about 6 to about 9.

63. A composition according to claim 1, wherein said composition is a ready-to-use composition.

64. A composition according to claim 1, wherein said composition is in the form of a liquid, cream, a gel, or in any other form suitable for keratinous fibers.

65. A composition according to claim 64, wherein said composition form may be optionally pressurized.

66. A method of dyeing keratinous fibers, comprising applying to said keratinous fibers for a sufficient time to develop a desired color at least dyeing composition comprising:
  (a) at least one enzyme of the laccase type;
  (b) at least one thickening polymer chosen from:
    (i) nonionic amphiphilic polymers comprising at least one fatty chain and at least one hydrophilic unit;
    (ii) anionic amphiphilic polymers comprising at least one hydrophilic unit and at least one fatty chain-containing unit;
    (iii) crosslinked homopolymers derived from monomers of acrylic acid;
    (iv) crosslinked homopolymers derived from monomers of 2-acrylamido-2-methylpropanesulphonic acid and crosslinked copolymers derived from monomers of acrylamide which are partially or completely neutralized;
    (v) homopolymers derived from monomers of ammonium acrylate and copolymers derived from monomers of (i) ammonium acrylate and (ii) acrylamide;
    (vi) homopolymers derived from monomers of dimethylaminoethyl methacrylate which is quaternized with methyl chloride and copolymers derived from monomers of (i) dimethylaminoethyl methacrylate which is quaternized with methyl chloride and (ii) acrylamide;
    (vii) nonionic guar gums;
    (viii) scleroglucan gums; and
    (ix) gums derived from plant exudates which comprise gum arabic, Ghatti gum, karaya gum and tragacanth gum; and
  (c) at least one oxidation dye.

67. A method of dyeing keratinous fibers according to claim 66, wherein said keratinous fibers are human keratinous fibers.

68. A method of dyeing keratinous fibers according to claim 67, wherein said human keratinous fibers are hair.

69. A method for dyeing keratinous fibers comprising the steps of:
  (a) storing a first composition,
  (b) storing a second composition separately from said first composition,
  (c) mixing the first composition with the second composition to form a mixture, and
  (d) applying said mixture to said keratinous fibers for a time sufficient to achieve a desired colouration,
    wherein said first composition comprises at least one oxidation dye and optionally comprises at least one thickening polymer, in a medium appropriate for keratinous fibers, and
    wherein said second composition comprises at least one enzyme of the laccase type and optionally comprises at least one thickening polymer, in a medium appropriate for keratinous fibers.

70. A multicompartment device or dyeing kit, comprising, a first compartment containing in a medium appropriate for dyeing, a composition (A) comprising at least one oxidation dye and a second compartment comprising a composition (B) comprising, in a medium appropriate for keratinous fibers, at least one enzyme of the laccase type wherein at least one of said composition (A) and composition (B) comprises at least one thickening polymer chosen from:
  (i) nonionic amphiphilic polymers comprising at least one fatty chain and at least one hydrophilic unit;
  (ii) anionic amphiphilic polymers comprising at least one hydrophilic unit and at least one fatty chain-containing unit;
  (iii) crosslinked homopolymers derived from monomers of acrylic acid;
  (iv) crosslinked homopolymers derived from monomers of 2-acrylamido-2-methylpropanesulphonic acid and crosslinked copolymers derived from monomers of acrylamide which are partially or completely neutralized;
  (v) homopolymers derived from monomers of ammonium acrylate and copolymers derived from monomers of (i) ammonium acrylate and (ii) acrylamide;
  (vi) homopolymers derived from monomers of dimethylaminoethyl methacrylate which is quaternized with methyl chloride and copolymers derived from monomers of (i) dimethylaminoethyl methacrylate which is quaternized with methyl chloride and (ii) acrylamide;
  (vii) nonionic guar gums;
  (viii) scleroglucan gums; and
  (ix) gums derived from plant exudates which comprise gum arabic, Ghatti gum, karaya gum and tragacanth gum.

* * * * *

UNITED STATES PATENT AND TRADEMARK OFFICE
CERTIFICATE OF CORRECTION

PATENT NO.    : 6,576,024 B1
DATED         : June 10, 2003
INVENTOR(S)   : Gérard Lang et al.

It is certified that error appears in the above-identified patent and that said Letters Patent is hereby corrected as shown below:

<u>Title page,</u>
Item [57], ABSTRACT,
Line 15, "quatemized" should read -- quaternized --.
Line 19, "origin):" should read -- origin); --.

<u>Column 16,</u>
Line 44, "*cladosporioildes*," should read -- *cladosporioides*, --.

<u>Column 18,</u>
Line 19, "moomers." should read -- monomers. --.
Line 53, "formula (3)" should read -- formula (3): --.
Line 60, "$CH_3$,and" should read -- $CH_3$, and --.

<u>Column 20,</u>
Lines 64 and 66, "claim 35," should read -- claim 1, --.

<u>Column 21,</u>
Line 31, "least dyeing" should read -- least one dyeing --.

<u>Column 22,</u>
Line 15, "colouration," should read -- coloration, --.

Signed and Sealed this

Seventh Day of October, 2003

JAMES E. ROGAN
*Director of the United States Patent and Trademark Office*